US008225682B2

(12) United States Patent
Schultz et al.

(10) Patent No.: US 8,225,682 B2
(45) Date of Patent: Jul. 24, 2012

(54) ACCELERATED WEATHERING TEST APPARATUS WITH CALIBRATION-ACCESS ASSEMBLY

(75) Inventors: Richard Schultz, Niles, IL (US); Richard D. Donato, Chicago, IL (US)

(73) Assignee: Atlas Materials Testing Technology, LLC, Chicago, IL (US)

(*) Notice: Subject to any disclaimer, the term of this patent is extended or adjusted under 35 U.S.C. 154(b) by 332 days.

(21) Appl. No.: 12/575,307

(22) Filed: Oct. 7, 2009

(65) Prior Publication Data

US 2011/0079071 A1    Apr. 7, 2011

(51) Int. Cl.
*G01N 17/00* (2006.01)
(52) U.S. Cl. .................. 73/865.6; 250/492.1; 356/243.1
(58) Field of Classification Search ............ 73/865.6; 250/492.1; 356/236; 49/41, 61, 68, 207
See application file for complete search history.

(56) References Cited

U.S. PATENT DOCUMENTS

| | | | |
|---|---|---|---|
| 1,554,025 A | 9/1925 | Peoples | |
| 3,072,079 A * | 1/1963 | Remke et al. | 109/58.5 |
| 3,500,682 A | 3/1970 | Newfield | |
| 3,536,370 A | 10/1970 | Evans et al. | |
| 3,576,125 A | 4/1971 | Kockott et al. | |
| 4,544,995 A | 10/1985 | Suga | |
| 4,665,627 A | 5/1987 | Wilde et al. | |
| 4,701,959 A * | 10/1987 | Asai et al. | 382/126 |
| 4,785,969 A * | 11/1988 | McLaughlin | 221/2 |
| D302,311 S | 7/1989 | Buck | |
| 5,136,778 A * | 8/1992 | Bell et al. | 29/806 |
| 5,206,518 A | 4/1993 | Fedor et al. | |
| 5,209,082 A | 5/1993 | Ha | |
| 5,266,272 A | 11/1993 | Griner et al. | |
| 5,535,889 A * | 7/1996 | Lin | 206/546 |
| 5,792,427 A | 8/1998 | Hugh et al. | |
| 5,854,433 A | 12/1998 | Patel et al. | |
| 5,893,489 A * | 4/1999 | Giarrante | 222/482 |
| 6,285,137 B1 * | 9/2001 | Grossman et al. | 315/291 |
| 6,581,333 B2 * | 6/2003 | Kimball | 49/504 |
| 6,679,128 B2 | 1/2004 | Wanek et al. | |
| 6,720,562 B2 | 4/2004 | Rathod et al. | |
| 6,872,936 B2 | 3/2005 | Rathod et al. | |
| 6,892,591 B2 | 5/2005 | Grossman et al. | |
| 6,946,652 B2 | 9/2005 | Rathod et al. | |
| 7,043,974 B2 | 5/2006 | Grossman et al. | |
| 2006/0027761 A1 * | 2/2006 | Schonlein et al. | 250/372 |
| 2008/0186158 A1 * | 8/2008 | Shoemaker et al. | 340/459 |

OTHER PUBLICATIONS

"QUV & Q-Sun—A Comparison of Two Effective Approaches to Accelerated Weathering & Light Stability Testing", Q-Lab Corporation, 2006.*
"QUV Accelerated Weathering Testers", Q-Lab Corporation, 2007.*
"Atlas UVTest Fluorescent/UV Instrument" Atlas Material Testing Technology, LLC, Oct. 12, 2009.*
Q-Panel Lab Products, Accelerated Weathering Tester Operating Manual for Model QUV/se, Serial Nos. 9X-XXXX-62-se and 9X-XXXX-62CE-se, revised Oct. 12, 1998, sections 1.0-14.0.
European Patent Office, Extended European Search Report issued in connection with EP Patent Application No. 10 18 2607, completed Dec. 15, 2010, received Mar. 22, 2011, 6 pages.

* cited by examiner

*Primary Examiner* — David Rogers
(74) *Attorney, Agent, or Firm* — Vedder Price P.C.

(57) ABSTRACT

An apparatus for accelerating the weathering effects on test specimens within a test chamber including a calibration-access assembly for replacing test sensors located within the apparatus with reference sensors when the apparatus door is closed. An improved sensor support assembly is also included. The calibration-access assembly from an improved location, facilitating superior irradiance detection. The calibration-access assembly including an aperture defined in the door of the apparatus and a shield connected to the door that is movable to permit or prevent access to sensors when the apparatus door is closed.

14 Claims, 6 Drawing Sheets

ACCELERATED WEATHERING TEST APPARATUS WITH CALIBRATION-ACCESS ASSEMBLY

FIELD OF THE INVENTION

The present invention relates to an apparatus for accelerating the weathering effects on test specimens, and more particularly, to an accelerated weathering apparatus having a calibration-access assembly for safely and conveniently accessing sensors for calibration.

BACKGROUND OF THE INVENTION

A conventional testing apparatus will frequently contain a sealed chamber that creates a controlled environment wherein testing may occur. It is often necessary to locate sensors within such a chamber to detect the conditions within the controlled environment. These sensors must be periodically calibrated for accuracy. Conventional apparatuses utilize several different configurations in an effort to provide access to the sensors for calibration. However, these conventional configurations suffer a number of drawbacks relating to sensor accuracy, operator safety, and accessibility.

Various attempts have been made to improve on the drawbacks associated with conventional testing apparatuses. Among these is U.S. patent to Evans et al., U.S. Pat. No. 3,536,370 issued Oct. 27, 1970; U.S. patent to Hugh et al., U.S. Pat. No. 5,792,427 issued Aug. 11, 1998; U.S. patent to Fedor et al., U.S. Pat. No. 5,206,518 issued Apr. 27, 1993; U.S. patent to Rathod et al., U.S. Pat. No. 6,946,652 issued Sep. 20, 2005; and an apparatus from Q-Lab Panel Corporation, called Q-U-V®.

Evans et al. is directed to an apparatus for carrying out processes in a controlled environment, and particularly for carrying out microbiological processes involving the production of dangerous pathogenic organisms. Evans et al. discloses an apparatus having a casing that includes three distinct chambers: a process chamber, a transfer chamber, and an instrument chamber. A transfer and exit liquid lock is fitted in the side of the casing. An internal wall of the lock juts into the transfer chamber and is open directly into the process chamber. A transfer well is let into the internal well from the transfer chamber. The arrangement is such that with sufficient liquid in the lock, the liquid seals the process chamber and the transfer chamber from each other and from the exterior of the casing. A sterilizing liquid is placed in lock and the transfer well is provided with a removable sealing cap to prevent loss of liquid by spillage.

An inlet lock is mounted in the casing to communicate between the exterior and the process chamber. The lock is a straight tube of bore sufficient for the passage of small containers or bottles. The lock contains an outer cap that may be removed to introduce instruments and sampling bottles into the process chamber. Control of the process is effected through the instrument and control panel located in the instrument chamber and glove ports. With the operator's left and right hands in the left and center gloves, the inner cap of the lock is removed and the object is transferred into the process chamber. Any container or instrument to be removed from the process chamber is dropped into the well associated with the transfer and exit liquid lock for retrieval by an operator. Thus, the structure and functionality of Evans et al. discloses a controlled environment apparatus wherein an inlet lock is used to safely introduce equipment into the process chamber and wherein a transfer and exit liquid lock is used to sterilize and safely retrieve equipment from a process chamber.

Hugh et al. describes a controlled atmosphere incubator and an improved incubator used to culture biological specimens. The controlled atmosphere incubator has an interior chamber surrounded by a heated water jacket. A glass access door of the chamber is directly heated by a clear, electrically conductive coating. The door is sealed against the perimeter of the opening by a readily replaceable gasket and is field reversible due to hinge mounting assemblies. The upper end of the cabinet includes a drawer for holding the various hardware components which are necessary in the implementation of the controlled atmosphere incubator. The drawer therefore allows easy maintenance and replacement of these components without necessitating the removal of panels. One such component located within the drawer is calibration circuitry for an infrared carbon dioxide sensor used by a microprocessor to calibrate the sensor. Thus, the structure and functionality of Hugh et al. appears to disclose a controlled atmosphere incubator having a drawer for isolation of hardware necessary for the control of the apparatus and calibration of the sensors.

Fedor et al. describes and relates to an accelerated weathering apparatus having a light source which irradiates onto specimens located in a specimen supporting wall which is located on the side of a test chamber. The output of the light source is controlled by independently adjustable control channels. The apparatus disclosed in Fedor et al. further includes light source detectors located on detector panels, which are located in the specimen supporting walls. The light source detectors detect irradiance existing in the test chamber and generate irradiance signals which are input to a controller. Each detector panel includes four openings, two of which are for ultraviolet detectors and two of which are for reference detectors. The light source detectors disclosed in Fedor et al. are only accessible by opening a pair of doors located on the sides of the apparatus. Thus, the structure and functionality of Fedor et al. appears to disclose test sensors that are mounted on detector panels located in specimen supporting walls, all of which are confined to the interior of the apparatus and accessible only by opening the apparatus doors.

Rathod et al. describes and relates to an apparatus for accelerated weathering testing specimens including discharge lamps as a concentrated light source for accelerating the deterioration of color, composition, and/or structure of test specimens. The apparatus further includes test modules that monitor the weathering test process from purportedly improved locations and detect the amount of irradiance to which specimens in the apparatus are exposed. The test modules are located in pockets formed within the doors for the test chamber such that the sensitive electronics of the modules are not exposed to the harsh environment within the test chamber. Rathod et al. further discloses a tank defining a test chamber, test modules, specimen holders, lamps, doors, and a moisture system. The doors have pockets formed therein for mounting test modules that house the test sensors and are replaceable with calibration modules housing calibration sensors for calibrating the system. Thus, the structure and functionality of Rathod et al. appears to disclose test and calibration sensors that are mounted in a pocket of a testing apparatus door and accessible without opening the apparatus door. A major disadvantage of this configuration is that the test and calibration modules fall out of the pockets when the door is opened resulting in an expensive accident. Another disadvantage is that the test and calibration modules must be removed from the door pockets before the door is opened. This is a serious hindrance and inconvenience to operation of the device.

The apparatus from Q-Lab Corporation describes and relates to an accelerated weathering tester designed to simulate the damaging effects of sunlight, dew, and rain on a test specimen. The apparatus includes a tank defining a test chamber, specimen holders, lamps, a main door, and a moisture system. The apparatus further includes florescent UV lamps to reproduce the effects of natural sunlight and a condensation mechanism to reproduce the effects of dew and rain. The Q-Lab apparatus also discloses irradiance sensors mounted on the specimen plane, behind the main door, that are only accessible by opening the main door. The main door further include safety interlocks. Thus, the structure and functionality of the Q-Lab Q-U-V accelerated weathering tester appears to disclose test sensors that are mounted on the specimen plane behind the main door.

While the above-discussed references offer unique configurations for accessing a sealed chamber, several drawbacks still exist.

With particular attention to Evans et al., it is noted that the transfer and exit lock contains a transfer well filled with sterilizing liquid. While this configuration is desirable for applications involving pathogenic organisms, it is ill-suited for applications involving sensitive electronic equipment. Specifically, removing sensitive electronic equipment, such as sensors, through a liquid-filled well would likely cause serious damage to the electronics, rendering them inoperable for their intended purpose.

A drawback associated with Hugh et al. is that the sensors are not mounted within the test chamber itself, but rather in the base of the moveable drawer. While this configuration makes the sensors accessible when the drawer is pulled out, it leads to serious sensor-alignment issues. Specifically, because the sensors are mounted on a moveable plane (the bottom of the drawer), it is difficult to ensure that the sensors obtain readings from the same disposition each time a reading is taken. This type of configuration negatively affects the sensors ability to return accurate readings.

With particular attention to Fedor et al. and the Q-Lab apparatus, it is noted that the test sensors are only accessible when an apparatus door is opened. Configurations requiring an apparatus door to be opened in order to remove or replace test sensors have several serious drawbacks. One such drawback is the possibility for operator injury. Utilizing either of these known configurations, an operator is required to first open an apparatus door in order to access the sensors. In so doing, the operator could be exposed to harmful ultra-violet radiation emanating from the apparatus light sources. For example, testing indicates that a conventional weathering apparatus, such as those disclosed in Fedor et al. and the Q-Lab apparatus, will breach the EN 61010-1 UV-safety standard within 30 seconds of operation when the apparatus door is in an open position.

Furthermore, and with respect to the Q-Lab device, the apparatus doors contain safety interlock mechanisms that must be manually defeated by short-circuiting or placing a magnet next to the proximity switch. Applying either of these methods to open the Q-Lab device's apparatus door would violate European Union safety regulations.

The configuration disclosed in Rathod et al. similarly suffers from several disadvantages described above. Additionally, other disadvantages of such a configuration include sensor alignment issues due to tolerance stackup, corrosion of connectors due to moisture breach, and difficult for operators to access the sensors.

Therefore, there is a need for an improved accelerated weathering apparatus that does not require the apparatus door to be open in order to access sensors, provides improved sensor accuracy, protects operators against harmful UV exposure, does not require a safety interlock to be defeated to access the sensors, protects connectors from corrosion, and has an ergonomic design facilitating convenient operator access to sensors.

The subject invention contemplates a new and improved accelerated weathering apparatus that overcomes all of the above-referenced problems, and others, and provides an optimal configuration for safely and conveniently accessing sensors.

DETAILED DESCRIPTION OF A PREFERRED EMBODIMENT OF THE INVENTION

Figure 1A:
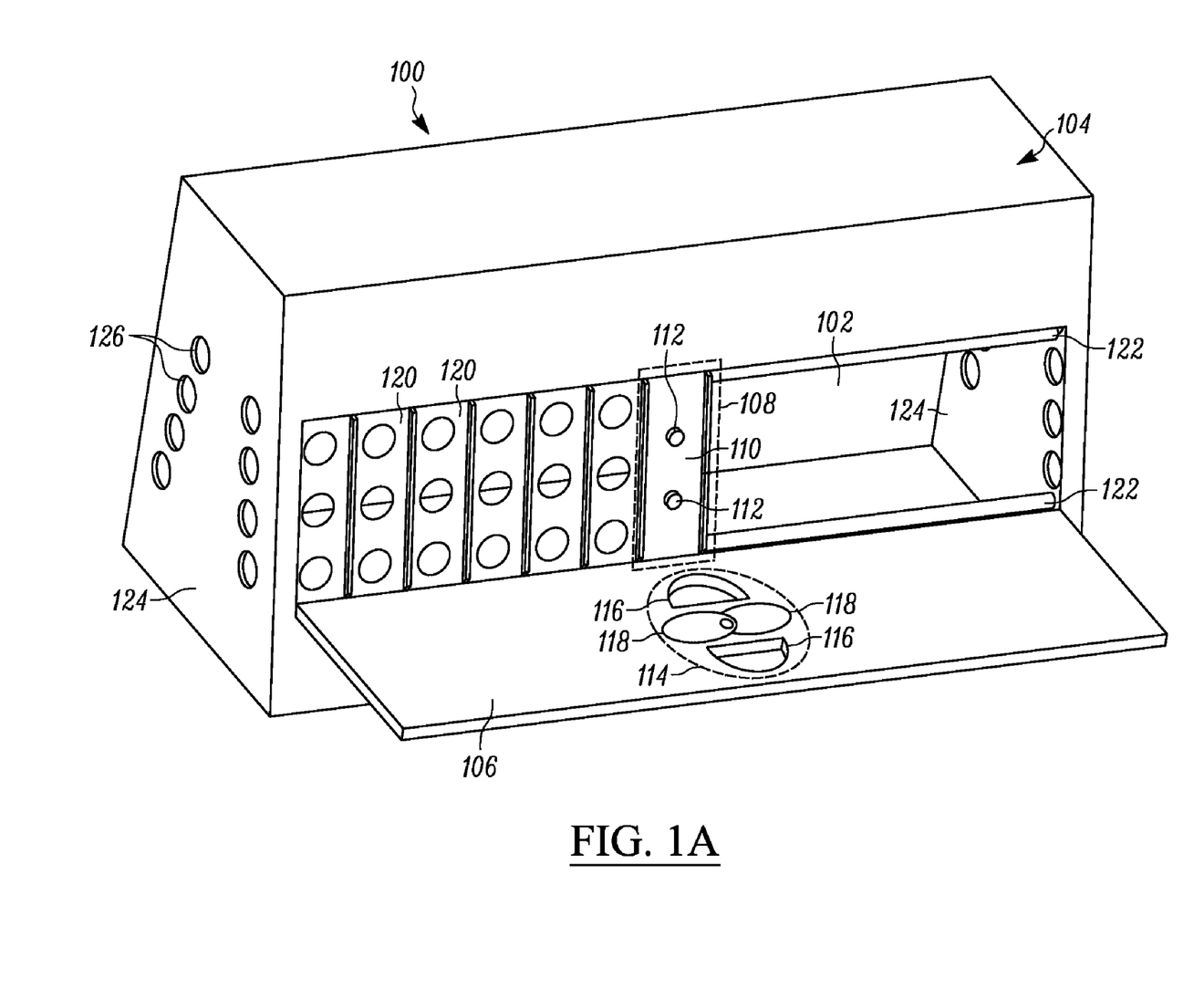
FIG. 1A is a detailed perspective view of an enclosure portion of an accelerated weathering apparatus in accordance with the present invention.

FIG. 1A shows a detailed perspective view of an enclosure portion 104 of an accelerated weathering apparatus 100 in accordance with the present invention. The apparatus 100 includes an enclosure 104 having at least one door 106 for access to a test chamber 102 defined within the enclosure 104. Only one door 106 will be discussed herein. However, it will be recognized by those of skill in the art that another door disposed in opposition may be identical in form and function. The test chamber 102 is generally defined within the enclosure 104. The enclosure 104 further includes an internal frame and enclosure sidewalls 124. A first door 106 is pivotally mounted to opposing enclosure sidewalls 124 and is in opposition to the second door (not shown), which is pivotally mounted to enclosure sidewalls 124. The door 106 provides access to the test chamber 102. A specimen mounting apparatus 232 (best shown in FIG. 2) is disposed within the test chamber 102 for supporting specimen holders 120.

In this embodiment, each specimen mounting apparatus 232 includes a bottom rail 232A and a top rail 232B, collectively defining a specimen supporting wall. The bottom rail is located at a first or outer position in the tank adjacent the pivot point of the door 106. The top rail is located at a second or inner position in the tank away from the top of the door near the center of the chamber 102 such that the mounting apparatus is defined on a plane inclined to the vertical axis. The specimen holders 120 are positioned on each specimen supporting wall for exposure to light, heat and liquid in an accelerated weathering environment. The specimen holders 120 are aligned side-by-side on the specimen supporting wall in a substantially continuous manner. In FIG. 1A, the specimen holders 120 are not depicted as extending the entire length of the door 106, so as to permit a better view of the test chamber 102. However, those having skill in the art will recognize that the specimen holders 120 may extend substantially along the length of the door 106 on the specimen supporting wall, provided that an opening is left so that sensors 112 may be exposed to the light source 226 (best shown in FIG. 2) for accurate irradiance detection.

A light source 226 is disposed within the test chamber 102 for producing light in the test chamber 102. While the light source 226 is not visible in FIG. 1A or FIG. 1B, apertures 126 for holding the light source 226 are clearly depicted within the enclosure sidewalls 124. In this embodiment, the light source 226 is shown as a plurality or array of lamps. In this embodiment, the plurality of lamps are disposed in first and second rows, each having four lamps. It will be recognized by those of skill in the art that the arrangement, configuration and number of lamps may be altered without departing from the present invention. The light source 226 is selected from the group of lamps that generate ultraviolet light in the UV-A, UV-B and UV-C ranges. For example, the lamps may be fluorescent, xenon or any other suitable type of lamp.

A calibration-access assembly 114 is formed in the door 106 in a generally medial location such that an aperture 116 is provided in the door so that sensors 112 may be interchangeably, removably disposed from a sensor-support assembly 108 (as will be discussed in further detail below) when a shield 118 is disposed in an open or second operative position.

The sensor support assembly 108 includes at least one sensor 112, a panel 110, and a pair of bars 122 that extend between opposing enclosure sidewalls 124. The bars 122 are offset such that the panel 110 is connected to, and extends between, the bars 122. In this manner, the panel 110 is discontiguous with and does not form any part of the specimen mounting apparatus 232. The test sensors 112 are interchangeably, removably connected to the panel 110 at a location corresponding to the light source 226 to detect irradiance in the test chamber 102 produced by the light source 226. The test sensors 112 can take any form well known in the art such as, for example, an optical photodiode.

The calibration-access assembly 114 includes at least one aperture 116 defined in the door 106 and at least one shield 118 connected to the door 106. In the embodiment depicted in FIG. 1A, the calibration-access assembly includes two apertures 116 and two shields 118, such that one aperture 116 and one shield 118 may be selectively in registration with each sensor 112. Each shield 118 is movable between first and second operative positions. When a shield 118 is in the first operative position, the aperture 116 is closed. In this position, the shield 118 prevents access to the panel 110 from the exterior of the apparatus 100. When a shield 118 is in the second operative position, the aperture 116 is opened. In this position, the shield 118 permits access to the panel 110 from the exterior of the apparatus 100. In this manner, the panel 110 (and thus the sensors 112) are accessible from the exterior of the apparatus 100 while the door 106 is in a closed position.

Figure 1B:
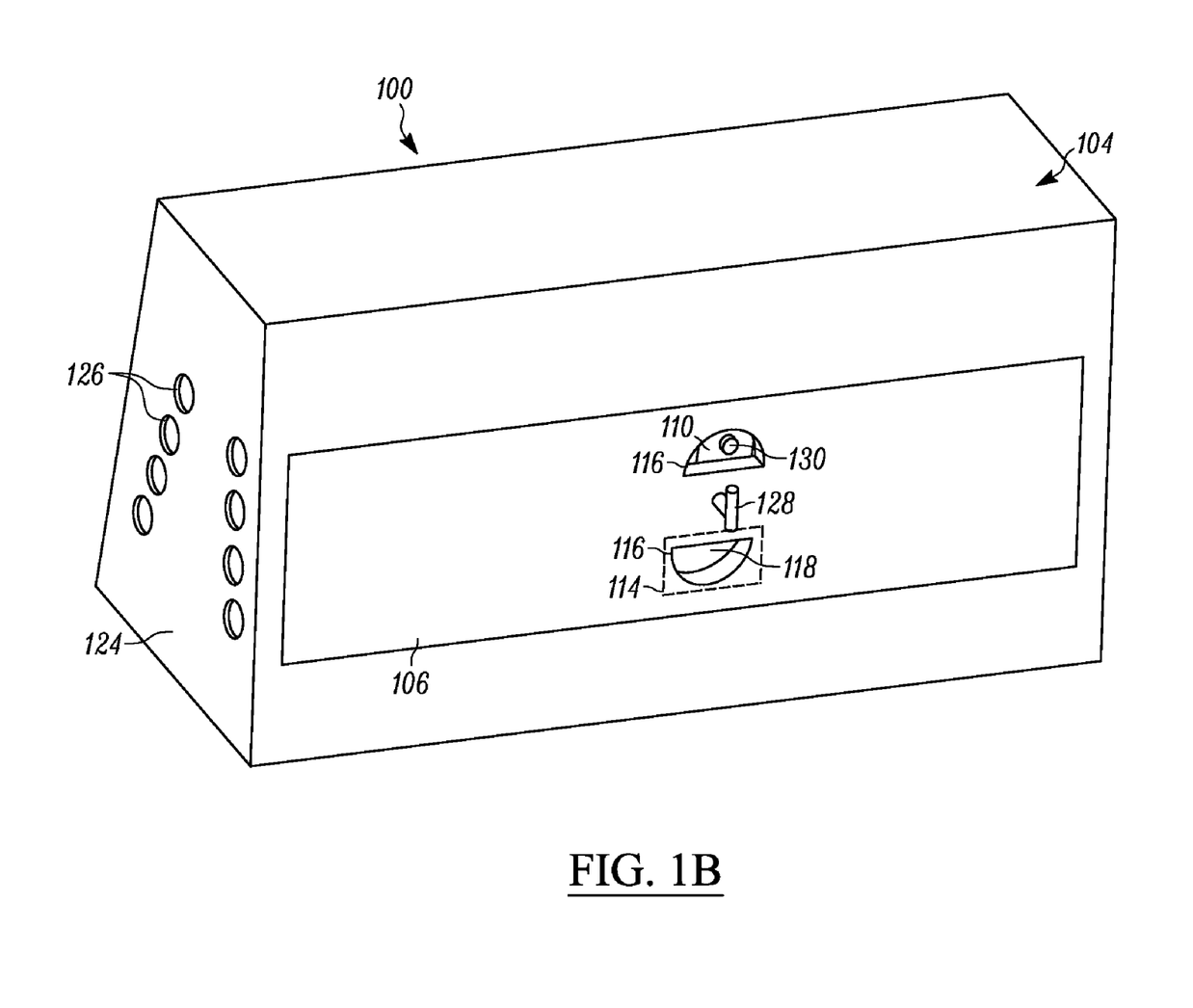
FIG. 1B is a detailed perspective view of the enclosure portion of the accelerated weathering apparatus showing a door in the closed position.
Figure 2:
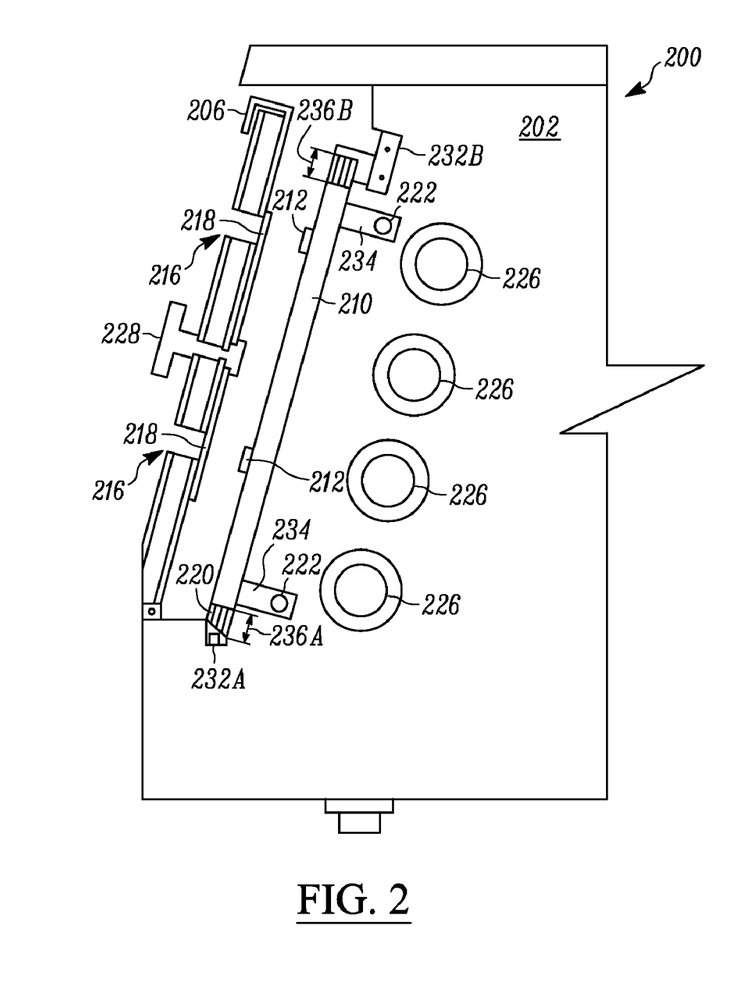
FIG. 2 is a partial cross-sectional view of an apparatus embodying the present invention.

FIG. 1B shows a detailed perspective view of the apparatus 100 depicted in FIG. 1A, wherein the door 106 is in a closed position and a reference sensor 130 has been removably connected to the panel 110 in place of a test sensor 112. In this embodiment, the apparatus 100 further includes a handle 128. The handle 128 is disposed on the exterior of the door 106 in a generally medial location corresponding to the location of the calibration-access assembly 114. The handle 128 is connected to each shield 118 such that movement of the handle 128 corresponds to movement of at least one shield 118. In the present embodiment, each shield 118 is disposed on the interior of the door 106, however, those having skill in the art will recognize that each shield 118 could be disposed on the exterior of the door 106 equally well.

Furthermore, FIG. 1B depicts an embodiment of the apparatus 100 wherein one shield (not visible in FIG. 1B) is disposed in the second operative position so as to permit access to the panel 110, while another shield 118 (the lower shield in FIG. 1B) is disposed in the first operative position so as to prevent access to the panel 110. When the apparatus 100 is in the embodiment shown in FIG. 1B, a reference sensor 130 is removably connected to the panel 110 in place of a test sensor 112. In one embodiment, the reference detector 130 may be, for example, of the cosine response receptor type, which accurately detects irradiance according to the cosine angle of the light impinging upon it. After obtaining a reading from the reference sensor 130, the apparatus 100 and/or test sensor 112 which was removed from the panel 110 can be adjusted to match the reading on the reference sensor 130, and re-inserted back onto the panel 110 in place of the reference sensor 130. In this manner, the test sensors 112 may be calibrated to ensure accurate detecting capabilities.

FIG. 2 is a partial cross-sectional view of an apparatus 200 embodying the present invention. While only one-half of the apparatus 200 is shown, it will be recognized by those of skill in the art that another half of the apparatus disposed in opposition may be identical in form and function. The apparatus 200 includes the enclosure 104 (best seen in FIG. 1A) defining a test chamber 202, a door 206, a specimen holder 220, light sources 226, a panel 210, and sensors 212. In this embodiment, the test chamber 202 has eight light sources 226 (four of which are shown). As discussed above, these light sources 226 may be florescent, xenon, or any other suitable ultraviolet light source. The specimen holder 220 is positioned on the specimen mounting apparatus 232, which includes a bottom rail 232A and a top rail 232B and is defined in a plane substantially parallel to the plane in which the light sources 226 are defined. The light sources 226 are positioned at a distance from the specimen holder 220, consequently providing the desired weathering effects.

In the embodiment depicted in FIG. 2, the door 206 has two apertures 216 and a handle 228. Furthermore, two shields 218 are depicted in their first operative positions such that they each prevent access to a panel 210 from the exterior of the door 206. The panel 210 has two sensors 212 interchangeably, removably mounted on it. In this embodiment, the panel 210 is connected to a pair of bars 222 via two brackets 234. The pair of bars 222 extend from one enclosure sidewall 124 to the other enclosure sidewall 124 and are operative to support the panel 210 and sensors 212 mounted thereon. A space 236A exists between the panel 210 and the bottom rail of the specimen mounting apparatus 232A such that the panel 210 is discontiguous with the specimen mounting apparatus. Similarly, a space 236B exists between the panel 210 and the top rail of the specimen mounting apparatus 236B.

Figure 3:
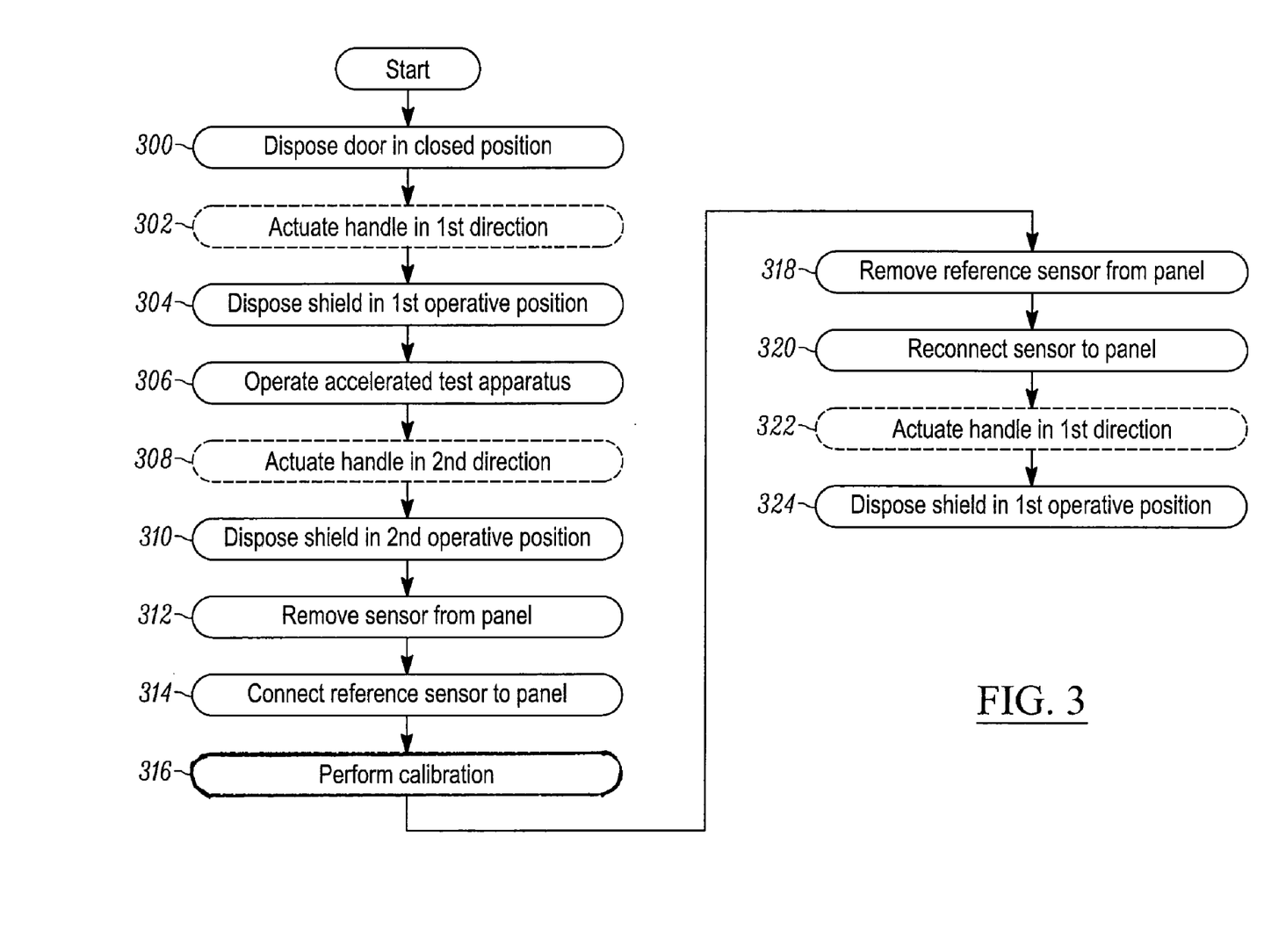
FIG. 3 is a flow chart diagram showing the sequential calibration procedure in accordance with one embodiment of the present invention.

FIG. 3 is a flowchart illustrating the calibration procedure for the present disclosure. During this procedure, a test sensor that is connected to the panel is removed and a reference sensor is substituted in its place. It will be recognized by one of skill in the art that the calibration procedure should be performed periodically as per industry standard. However, an operator may calibrate the machine at any time during a test. At block 300 the door is disposed in a closed position. Next, at block 304, a shield is disposed in its first operative position such that the panel is inaccessible from the exterior of the door. Block 302 represents an optional step wherein a handle on the exterior of the door is actuated in a first direction to dispose the shield in its first operative position. At block 306 the accelerated weathering apparatus is operated to expose test specimens to ultra-violet light. At block 310 the shield is disposed in a second operative position such that the panel is accessible from the exterior of the door. Block 308 also represents an optional step wherein the handle is actuated in a second direction to dispose the shield in the second operative position. At block 312 the test sensor is removed from the panel. At block 314 a reference sensor is connected to the panel in place of the test sensor. At block 316 calibration is performed. At block 318 the reference sensor is removed from the panel. At block 320 the test sensor is reconnected to the panel in place of the reference sensor. At block 324 the shield is disposed back into its first operative position. Block 322 represents an optional step wherein the handle is once again actuated in the first direction to dispose the shield in its first operative position.

Figure 4:
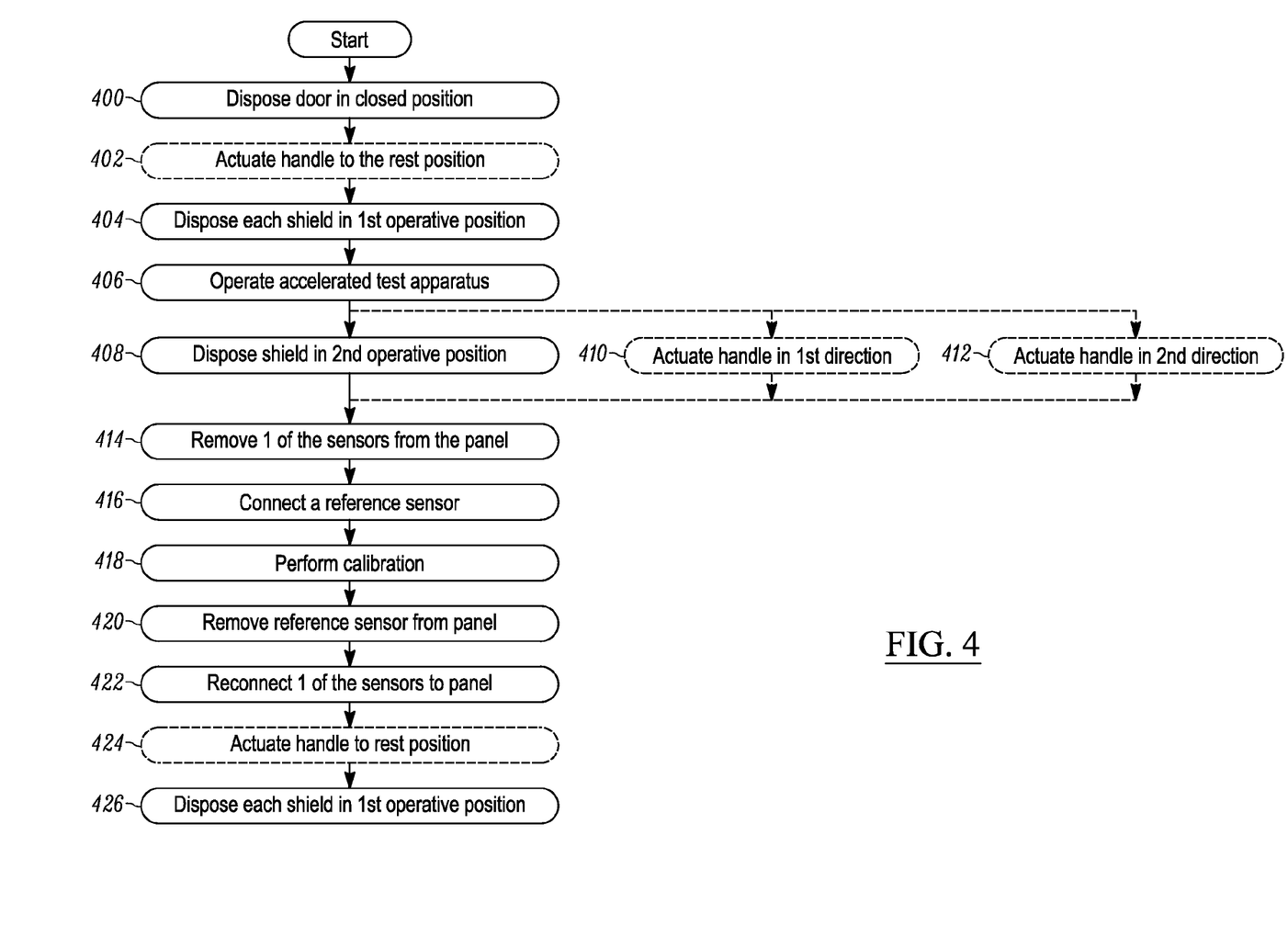
FIG. 4 is a flow chart diagram showing the sequential calibration procedure in accordance with another embodiment of the present invention.

FIG. 4 is a flowchart illustrating another embodiment of the calibration procedure wherein a handle is operative to dispose a plurality of shields in either their first or second operative positions. At block 400 the door is disposed in the closed position. At block 404 each shield is disposed in its first operative position. Block 402 represents an optional step wherein the handle is actuated to the rest position to dispose each shield in its first operative position. At block 406 the accelerated weathering apparatus is operated. At block 408 a shield is disposed in its second operative position. Block 410 represents an optional step wherein the handle is actuated in a first direction to dispose one shield from its first operative position to its second operative position while the other shields remain disposed in first operative positions. Similarly, block 412 represents an optional step wherein the handle is actuated in a second direction to dispose an other shield from its first operative position to its second operative position while the other shields remain disposed in first operative positions. At block 414 one of a plurality of sensors is removed from the panel. At block 416 a reference sensor is connected to the panel in place of the removed one of the plurality of sensors. At block 418 calibration is performed. At block 420 the reference sensor is removed from the panel. At block 422 one of the plurality of sensors is reconnected to the panel in place of the reference sensor. At block 426 each shield is disposed in its first operative position. Block 424 represents an optional step wherein the handle is once again actuated to the rest position to dispose each shield in its first operative position.

Figure 5:
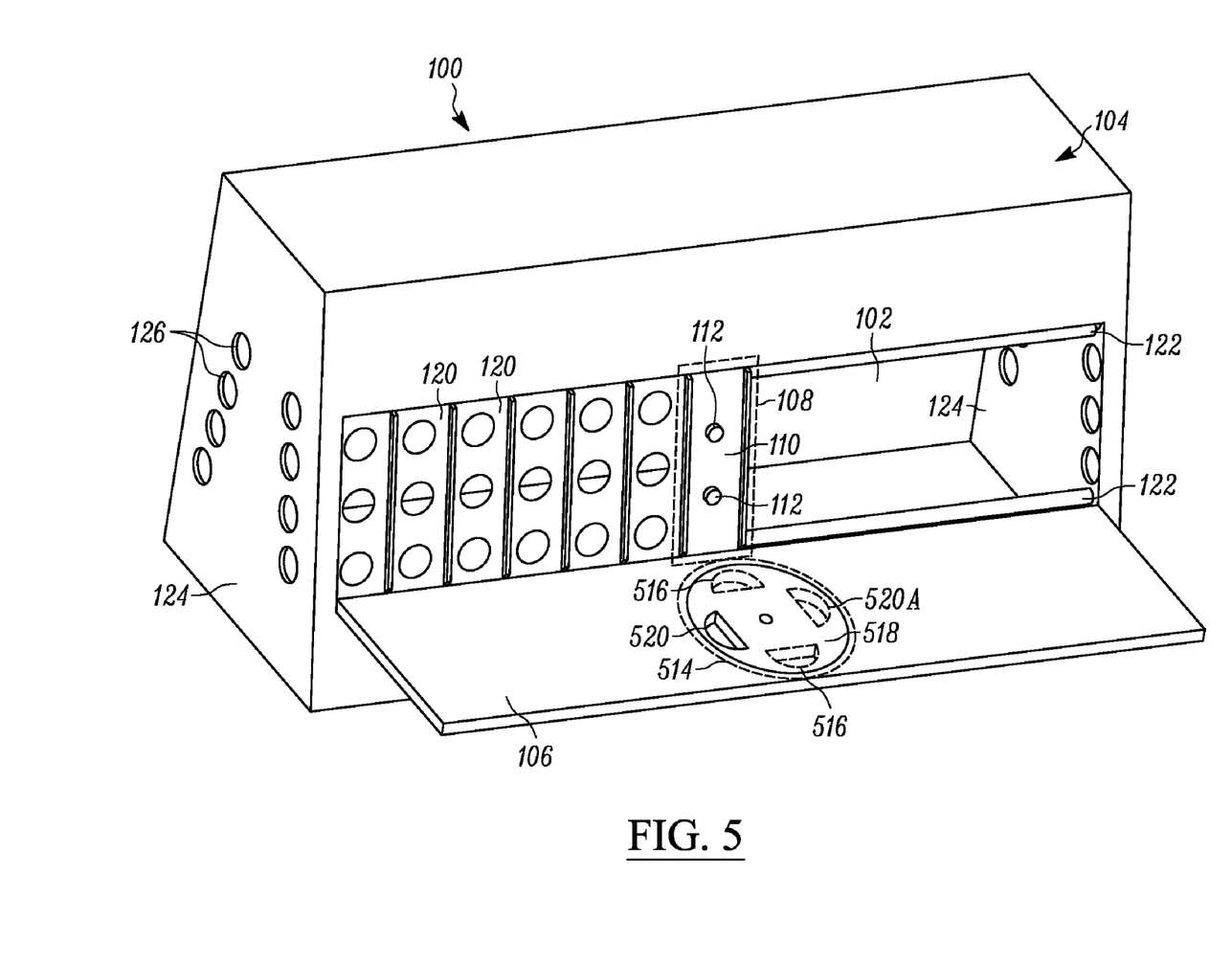
FIG. 5 is a detailed perspective view of the enclosure portion of the accelerated weathering apparatus showing another embodiment of the calibration-access assembly.

FIG. 5 shows a detailed perspective view of an another embodiment of the accelerated weathering apparatus 100 of FIG. 1A. In this embodiment, the calibration access assembly 514 includes two apertures 516 defined in the door 106 and one shield 518 connected to the door 106. The shield 518 includes at least one shield window 520 defined in the shield 518, such that one shield window 520 may be selectively in registration with one aperture 516 for accessing at least one sensor 112. The shield 518 is movable between first and second operative positions. When the shield 518 is in the first operative position (as shown in FIG. 5), the apertures 516 are closed. In this position, the shield 518 prevents access to the panel 110 from the exterior of the apparatus 100. When the shield 518 is in the second operative position, at least one aperture 516 is opened. In this position, the shield 518 permits access to the panel 110 from the exterior of the apparatus while the door 106 is in a closed position. It will be recognized by those of skill in the art that any number of optional shield windows 520a may be defined in the shield 518 to correspond to the total number of apertures 516 defined in the door 106. Furthermore, any other configuration might be desirable in other applications.

The invention is not limited to the particular details of the apparatus for methods shown or described and other modifications and applications may be contemplated. Certain other changes may be made in the above-described apparatus without departing from the true spirit and scope of the invention here involved. For example, an embodiment of the present invention may instead, or additionally, include software to perform some or all of the functions. It is intended, therefore, that the subject matter of the above depiction shall be interpreted as is illustrative and not in a limiting sense.

What is claimed is:

1. An accelerated weathering test apparatus comprising a test chamber defined within an enclosure for exposing a specimen to a light source, the accelerated weathering test apparatus further comprising:
a door connected to the enclosure that is movable between an open position that permits access to the test chamber and a closed position that prevents access to the test chamber;
a sensor-support assembly disposed in the test chamber including a panel and a sensor removably connected to the panel for exposure to the light source; and
a calibration-access assembly including an aperture defined in the door and a shield connected to an interior of the door that is movable between a first operative position that prevents access to the panel and a second operative position that permits access to the panel, wherein a reference sensor is removably connected to the panel in place of the sensor when the door is disposed in the closed position and the shield is disposed in the second operative position, wherein the accelerated weathering test apparatus further comprises a specimen mounting apparatus disposed within the test chamber for supporting a specimen holder and the sensor-support assembly further comprises a pair of bars that extend between opposing enclosure sidewalls, wherein the bars are offset such that the panel is connected to and extends between the bars and is discontiguous with the specimen mounting apparatus.

2. An accelerated weathering test apparatus comprising a test chamber defined within an enclosure for exposing a specimen to a light source, the accelerated weathering test apparatus further comprising:
a door connected to the enclosure that is movable between an open position that permits access to the test chamber and a closed position that prevents access to the test chamber;
a sensor-support assembly disposed in the test chamber including a panel and a plurality of sensors removably connected to the panel for exposure to the light source;
a calibration-access assembly in registration with each of the plurality of sensors including:
an aperture defined in the door and a shield connected to the door that is movable between a first operative position that prevents access to the sensor and a second operative position that permits access to the sensor; and
a handle connected to each shield, the handle disposed on an exterior of the door such that movement of the handle corresponds to movement of each shield, wherein a reference sensor is removably connected to the panel in place of one of the plurality of sensors when the door is disposed in the closed position and one of the shields is disposed in the second operative position, wherein one shield moves from its first operative position to its second operative position when the handle is actuated in a first direction and other shields remain disposed in first operative positions.

3. The accelerated weathering test apparatus as recited in claim 2, wherein the handle selectively moves one of the shields to the second operative position.

4. The accelerated weathering test apparatus as recited in claim 2, wherein the accelerated weathering test apparatus further comprises a specimen mounting apparatus disposed within the test chamber for supporting a specimen holder and the sensor-support assembly further comprises a pair of bars that extend between opposing enclosure sidewalls, wherein the bars are offset such that the panel is connected to and extends between the bars and is discontiguous with the specimen mounting apparatus.

5. The accelerated weathering test apparatus as recited in claim 2, wherein each shield is disposed on an interior of the door.

6. The accelerated weathering test apparatus as recited in claim 2, wherein one shield moves from its first operative position to its second operative position when the handle is actuated in a first direction while another shield remains disposed in its first operative position and the another shield moves from its first operative position to its second operative position when the handle is actuated in a second direction while the one shield remains disposed in its first operative position.

7. The accelerated weathering test apparatus as recited in claim 6, wherein the first and second directions are opposite with respect to a rest position.

8. A method of calibrating an accelerated weathering test apparatus comprising a test chamber defined within an enclosure for exposing a specimen to a light source, a door connected to the enclosure that is movable between an open position that permits access to the test chamber and a closed position that prevents access to the test chamber, a sensor-support assembly disposed in the test chamber including a panel and a sensor removably connected to the panel for exposure to the light source and detecting irradiance, and a calibration-access assembly including an aperture defined in the door and a shield connected to the door that is movable between a first operative position that prevents access to the panel and a second operative position that permits access to the panel, the method comprising the steps of:
 disposing the door in the closed position;
 disposing the shield in the first operative position;
 operating the accelerated weathering test apparatus;
 disposing the shield in the second operative position;
 removing the sensor from the panel;
 connecting a reference sensor to the panel;
 performing calibration;
 removing the reference sensor from the panel;
 reconnecting the sensor to the panel; and
 disposing the shield in the first operative position.

9. The method of calibrating an accelerated weathering test apparatus as recited in claim 8, wherein the accelerated weathering test apparatus further comprises a specimen mounting apparatus disposed within the test chamber for supporting a specimen holder and the sensor-support assembly further comprises a pair of bars that extend between opposing enclosure sidewalls, wherein the bars are offset such that the panel is connected to and extends between the bars and is discontiguous with the specimen mounting apparatus.

10. The method of calibrating an accelerated weathering test apparatus as recited in claim 8, wherein the accelerated weathering test apparatus further comprises a handle connected to the shield, the handle disposed on an exterior of the door such that movement of the handle corresponds to movement of the shield, the method further comprising the steps of:
 actuating the handle in a first direction to dispose the shield in the first operative position; and
 actuating the handle in a second direction to dispose the shield in the second operative position.

11. A method of calibrating an accelerated weathering test apparatus comprising a test chamber defined within an enclosure for exposing a specimen to a light source, a door connected to the enclosure that is movable between an open position that permits access to the test chamber and a closed position that prevents access to the test chamber, a sensor-support assembly disposed in the test chamber including a panel and a plurality of sensors removably connected to the panel for exposure to the light source and detecting irradiance, a calibration-access assembly in registration with each of the plurality of sensors including an aperture defined in the door and a shield connected to the door that is movable between a first operative position that prevents access to the panel and a second operative position that permits access to the panel, and a handle connected to each shield, the method comprising the steps of:
 disposing the door in the closed position;
 disposing each shield in the first operative position;
 operating the accelerated weathering test apparatus;
 disposing one shield in the second operative position;
 removing one of the plurality of sensors from the panel;
 connecting a reference sensor to the panel in place of the removed one of the plurality of sensors;
 performing calibration;
 removing the reference sensor from the panel;
 reconnecting one of the plurality of sensors to the panel; and
 disposing the shield in the first operative position.

12. The method of calibrating an accelerated weathering test apparatus as recited in claim 11, further comprising a handle disposed on an exterior of the door such that movement of the handle corresponds to movement of each shield wherein each shield is disposed in the first operative position when the handle is in a rest position, the method further comprising the steps of:
 actuating the handle to the rest position to dispose each shield in the first operative position;
 actuating the handle in a first direction to move one shield from its first operative position to its second operative position while other shields remain disposed in first operative positions; and
 actuating the handle in a second direction to move an other shield from its first operative position to its second operative position while the other shields remain disposed in first operative positions.

13. The method of calibrating an accelerated weathering test apparatus as recited in claim 12, wherein the first and second directions are opposite with respect to the rest position.

14. The method of calibrating an accelerated weathering test apparatus as recited in claim 11, wherein the accelerated weathering test apparatus further comprises a specimen mounting apparatus disposed within the test chamber for supporting a specimen holder and the sensor-support assembly further comprises a pair of bars that extend between opposing enclosure sidewalls, wherein the bars are offset such that the panel is connected to and extends between the bars and is discontiguous with the specimen mounting apparatus.

* * * * *